United States Patent
Greenwald et al.

(10) Patent No.: US 7,482,818 B2
(45) Date of Patent: Jan. 27, 2009

(54) SYSTEMS AND METHODS FOR DETECTING THE PRESENCE AND/OR ABSENCE OF A SOLID LIQUID OR GAS

(75) Inventors: Shlomo Greenwald, Ithaca, NY (US); Zipora Greenwald, Ithaca, NY (US)

(73) Assignee: Greenwald Technologies, LLC, Ithaca, NY (US)

( * ) Notice: Subject to any disclaimer, the term of this patent is extended or adjusted under 35 U.S.C. 154(b) by 0 days.

(21) Appl. No.: 11/735,784

(22) Filed: Apr. 16, 2007

(65) Prior Publication Data
US 2007/0241286 A1 Oct. 18, 2007

Related U.S. Application Data

(60) Provisional application No. 60/744,951, filed on Apr. 17, 2006.

(51) Int. Cl.
*G01R 27/32* (2006.01)
*G01N 27/00* (2006.01)
*G01S 13/08* (2006.01)

(52) U.S. Cl. ................ 324/639; 324/640; 324/71.1; 342/124

(58) Field of Classification Search .......... 324/639, 324/640, 71.1; 342/124
See application file for complete search history.

(56) References Cited

U.S. PATENT DOCUMENTS

| | | | | | |
|---|---|---|---|---|---|
| 4,782,282 | A | * | 11/1988 | Bachman | 324/686 |
| 5,351,036 | A | * | 9/1994 | Brown et al. | 342/124 |
| 5,934,997 | A | * | 8/1999 | Nelson et al. | 460/7 |
| 6,169,394 | B1 | * | 1/2001 | Frazier et al. | 324/71.4 |
| 6,691,563 | B1 | * | 2/2004 | Trabelsi et al. | 324/640 |
| 7,068,050 | B2 | * | 6/2006 | Steele et al. | 324/640 |
| 2004/0119637 | A1 | * | 6/2004 | Angal et al. | 342/124 |

* cited by examiner

*Primary Examiner*—Timothy J Dole
(74) *Attorney, Agent, or Firm*—Brown + Michaels, PC

(57) ABSTRACT

Systems and methods are described for detecting the presence and/or absence of a solid, liquid or gas which utilize an RF energy emitter and RF energy detector for determining whether a solid, liquid or gas is present within a defined physical space. More specifically, an RF energy emitter is provided at a first side of a solid, liquid or gas transmission channel and an RF energy receiver/detector is provided at an opposite side of the solid liquid or gas fluid channel. The RF energy emitter either continuously or periodically emits RF energy which in the preferred exemplary embodiment is in the high-frequency or more preferably ultrahigh frequency signal range. The amount of detected RF energy transferred across the channel is used in determining the presence and/or absence of a solid, liquid or gas.

8 Claims, 14 Drawing Sheets

SYSTEMS AND METHODS FOR DETECTING THE PRESENCE AND/OR ABSENCE OF A SOLID LIQUID OR GAS

REFERENCE TO RELATED APPLICATIONS

This application claims priority to U.S. Provisional Application No. 60/744,951, filed Apr. 17, 2006, entitled "Liquid/Air Bubble/Solid Objects Detector." The benefit under 35 USC §119(e) of the United States provisional application is hereby claimed, and the aforementioned application is hereby incorporated herein by reference.

BACKGROUND OF THE INVENTION

1. Field of the Invention

The present invention relates generally to the field of automated sensing systems and methods. More specifically, the present invention is directed to systems and methods for detecting the presence and/or absence of a solid, liquid or gas utilizing an RF energy emitter and RF energy detector for determining whether a solid, liquid or gas is present within a defined physical space between the RF energy emitter and RF energy detector.

2. Description of the Related Art

A wide variety of conventional systems and methods are available for determining whether a solid, liquid or gas is present within a specified physical space. For example, conventional detectors include such devices and techniques as mechanical fluid level sensors, product sensors and counters. Conventional systems utilizing mechanical sensors for fluid level detection often employ a float mechanism and a related sensor or visible indicator for identifying a location of the mechanical float or liquid level. One problem associated with conventional sensing systems and methods which rely upon mechanical structures or floating bodies for determining fluid level is that they are subject to mechanical breakdown as a result of corrosion and/or fouling of the mechanical float structure with debris and/or mineral or chemical deposits. In alternate approaches which rely upon a fluid level sensing channel, the channel itself is subject to corrosion and/or fouling with debris and/or mineral or chemical deposits.

In many vending and other similar dispensing applications there is a need to know when the system has run out of product. One of these applications is in the beverage industry. Specifically, for example, in post-mix beverage dispensers where it is desired to know when the bag of the concentrated liquid beverage is out of product there may be a need to sense fluid levels and/or the presence or absence of the product. Currently, in typical conventional post-mix dispensers, a vacuum sensor is typically used to detect when the concentrate liquid bag is out of product. This method has numerous disadvantages;

- The sensor must come into contact with the beverage concentrate liquid;
- It works only for systems where the concentrated liquid dispensing pump is powerful enough to create a vacuum, when the bag is out of product, and trigger the sensor.
- It has a long response time during which water is dispensed.

A second method that is used to detect if the concentrated liquid bag is out of product relies upon the use of one or more electrode pairs and measurement of the electrical conductivity or resistance between the electrodes for the purpose of sensing fluid level or the presence and/or absence of the fluid at a particular level. This method also has the disadvantage that it is necessary to have the two electrodes come in contact with the concentrated liquid and if the electrodes are not kept clean, the sensor will malfunction.

Yet another conventional approach relies upon the use of an optical sensor. However, this technique will not work when the tubing through which the product travels is opaque, or when the liquid leaves residue on the inner walls of the tubing thereby blocking the sensor light. Also, most of the Silicon or Tigon tubing that are used reflects or absorb most of the sensor infrared light and the sensitivity and resolution of devices which rely upon this technique is therefore very poor. Furthermore, the performance of optical sensors can be degraded by the presence of debris, which is often encountered in packaging and manufacturing environments. For example, in the pharmaceutical industry dust from the tablets can cause erroneous readings from optical sensing devices.

Accordingly, typical conventional mechanical, optical or electronic sensors for detecting the presence of a liquid in implementations for vending machines such as coffee dispensers and the like are inherently prone to degradation and breakdown and there remains a need for improvement or replacement of these conventional devices. Mechanical floating structures have been used for sensing fluid levels in a wide variety of devices including automated dispensers for coffee and other liquids as well as fuel tanks and ink tanks. Mechanical sensors have also been used in a wide variety of applications such as, product detectors and counters including solid pharmaceutical product sensors and counters. All of these known conventional mechanical systems for detecting the presence of a solid, liquid or gas are subject to degradation in performance over time as a result of the mechanical breakdowns noted above.

More recently, other conventional approaches for sensing the presence and/or absence of a solid, liquid or gas include the use of ultrasonic detectors for making the determination of whether a solid, liquid or gas is present. One shortcoming of these conventional systems is that an ultra sonic detector for a solid, liquid or gas requires a complicated emitter and detector structure as well as a complex signal analyzer for examining the returned signal. Accordingly, although this approach is not necessarily subject to the mechanical breakdown problems associated with conventional mechanical sensors for determining the presence of a solid liquid or gas, this alternate conventional technique has its own shortcomings and requires a significant economic expenditure for the manufacture of the ultrasonic detecting system. Furthermore, ultrasonic detectors are not very suitable for use as a detection mechanism when there is an air gap between the product to be detected and the ultrasonic emitter.

Accordingly, there remains a need in the field for an accurate and reliable system and method for detecting the presence of a solid liquid or gas which is not subject to the potential breakdowns associated with conventional mechanical devices and is relatively inexpensive compared with the known ultrasonic techniques for sensing the presence of a solid, liquid or gas.

SUMMARY OF THE INVENTION

In accordance with various embodiments of the present invention, systems and methods are described for detecting the presence and/or absence of a solid, liquid or gas which utilize an RF energy emitter and RF energy detector for determining whether a solid, liquid or gas is present within a defined physical space. More specifically, in accordance with a first exemplary embodiment of the present invention, an RF energy emitter is provided on a first side of a solid, liquid or gas transmission channel and an RF energy receiver/detector is provided at an opposite side of the solid liquid or gas fluid channel.

The RF energy emitter either continuously or periodically emits RF energy which in the preferred exemplary embodiment is in the high-frequency or more preferably ultrahigh frequency signal range. For example, in exemplary embodiment, the RF energy transmission source provides at least a primary output of approximately 2.4 GHz. Those of ordinary skill in the art will appreciate that a wide range of transmission frequencies are possible for utilization in conjunction with the systems and methods of the present invention. The RF energy detector mechanism is located across the solid liquid or gas transmission channel.

In accordance with the preferred exemplary embodiment, the RF energy emitter and RF energy detector structures are preferably located within a housing that is comprised of a conductive material, or which is shielded with conductive material for the purpose of limiting spurious emissions from the device. The shielded structure also limits extraneous RF noise thereby improving accuracy and the ability of the system to achieve finer resolution. Although any conductive housing is suitable for providing the shielding structure, in order to reduce manufacturing costs, it is preferred that the housing is embodied as a plastic structure having internal sidewalls coated with a material such as, for example, chrome. It should be recognized that other conductive materials will also be suitable and it is preferred that the thickness of the conductive shielding member be at least approximately a few skin depths at the primary RF emission frequency. Machined aluminum may also be used for the housing.

The presence and/or absence of a solid, liquid or gas within the channel or physical space between the RF energy emitter and RF energy detector alters the amount of RF energy received by the RF energy detector and this information may be utilized to determine whether or not the solid, liquid or gas is present within the channel or other defined space. Circuitry is provided for determining whether a solid, liquid or gas is present, and/or absent in the space between the RF energy emitter and RF energy receiver/detector.

There is a very wide range of applications for the systems and methods described herein which are able to determine whether a solid, liquid, or gas passes through the space between the RF energy emitter and RF energy receiver/detector. Applications for these types of alternate embodiments include automated counting mechanisms which may be used for counting pills and the like as well as flow rate detection systems and methods as well as fluid level sensors.

In accordance with a first preferred exemplary embodiment of the present invention, a simple RF diode detector such as, for example, a Schottky diode, is utilized for determining whether or not a solid, liquid or gas is present in the channel between the RF energy emitter and the RF energy detector. In such an embodiment, a comparator is preferably used for providing an appropriate signal level triggering point for ascertaining whether or not the solid, liquid or gas is present in the channel between the RF energy emitter and RF energy detector. Alternatively, instead of utilizing a simple diode mechanism, a commercial RF detector may be utilized and the output of this RF detector is transmitted to a comparator with an appropriate comparison signal level for ascertaining the presence and/or absence of a solid liquid or gas within the channel between the RF energy emitter and RF detector.

The inventors of the subject matter described in the instant application have discovered that there are a wide variety of potential uses for the present innovations. For example, the technology described herein may be useful in such applications as fluid level sensors of any type including fuel tank level indicators, ink cartridge ink level detectors, vending machines for such things as coffee and other fluids. The systems and methods of the present invention may also be used for such things as automated product sensors and counters including solid pharmaceutical and nutraceutical detectors and counters. The systems and methods of the present invention may also be used for such things as fluid flow rate sensors and air bubble detection in IV systems and the like.

Currently in hospitals in about 50% of the cases the medical staff is using an infusion pump, even in situations where gravity infusion can be utilized. In these cases the medical staff is using infusion pump primarily to set the desired flow rate and to alarm the staff when there is no flow (for example; the patient is pinching the tube) or the infusion liquid bag is empty or out of product. The automated sensor systems and methods of the present invention can provide a simple device at a fraction of cost of an infusion pump that will provide the same desired functions.

In such an implementation, this device will preferably include a single solid, liquid or gas detector which will be mounted on the outside of the drip-cup, located at the top of the infusion set. A controller with digital display is preferably also provided and the system is able to sound an alarm if an incorrect flow rate is detected. The system will count the number of the drops falling through into a drip cup and convert it to the flow rate in mL/hr using a known conversion factor. Using the measured and displayed flow rate, the nurse will be able to adjust the flow rate that is required, using the pinch wheel, for example, at the same accuracy as with an infusion pump. As noted above, in case the flow stops or if the flow rate falls outside of a desired range, the device will sound an alarm.

In yet another alternate embodiment, the system provides a simple device that is able to stop the infusion process if a large and potentially harmful air bubble is detected. For example, conventional infusion pumps are stopped if the air bubbles are detected which are 0.1 CC or larger. In this alternate embodiment, the patient infusion system preferably includes a processor or controller and a small, solenoid operated pinch valve and alarm. In this embodiment, when the system detects an air bubble equal or larger to the allowed volume it will activate the pinch valve which will pinch the infusion tubing and stop the flow. The system also preferably activates an alarm. In addition the air-bubble device will be able to measure the total accumulated air bubble volume, when each one of them is smaller than the critical volume, administrated to the patient during the time of the infusion.

Some advantages of this embodiment include:

A reduced cost which is only a fraction of an infusion pump;

The system is physically small in size;

The system uses very little power and can be operated by a battery charged by a photovoltaic charger and it is not required to be connected to a power outlet.

Because they are small in size they can be mounted directly on the infusion pole and easily moved with the patient.

They are very simple to operate.

In yet another alternate embodiment, the systems and methods of the present invention may be used in conjunction with dialysis machines.

Specifically, the solid liquid or gas sensor of the present invention can be used in dialysis systems to detect the present of gas bubbles in the recirculated blood. The solid liquid or gas sensor can also be used to detect solid objects floating in the recirculation blood such as, for example, a blood clot.

Yet another alternate embodiment of the present invention is directed to the medication packaging industry. In this industry, an optical sensor is currently the most common conventional solid product detector. The optical sensor is conventionally used to count and verify the number of dispensed medication units. During the packaging process dust is created which after a relatively short period causes the optical sensors to fail at an unaccepted rate as the dust builds up. This requires stopping the packaging process and cleaning the system periodically. The systems and methods of the present invention are not affected by the dust therefore it will allow running the packaging system for long periods without stopping and increasing the system efficiency.

Those skilled in the art will appreciate that there are a wide variety of other applications for the solid, liquid and/or gas detection systems and methods of the present invention.

DETAILED DESCRIPTION OF THE PRESENTLY PREFERRED EMBODIMENTS

Figure 1:
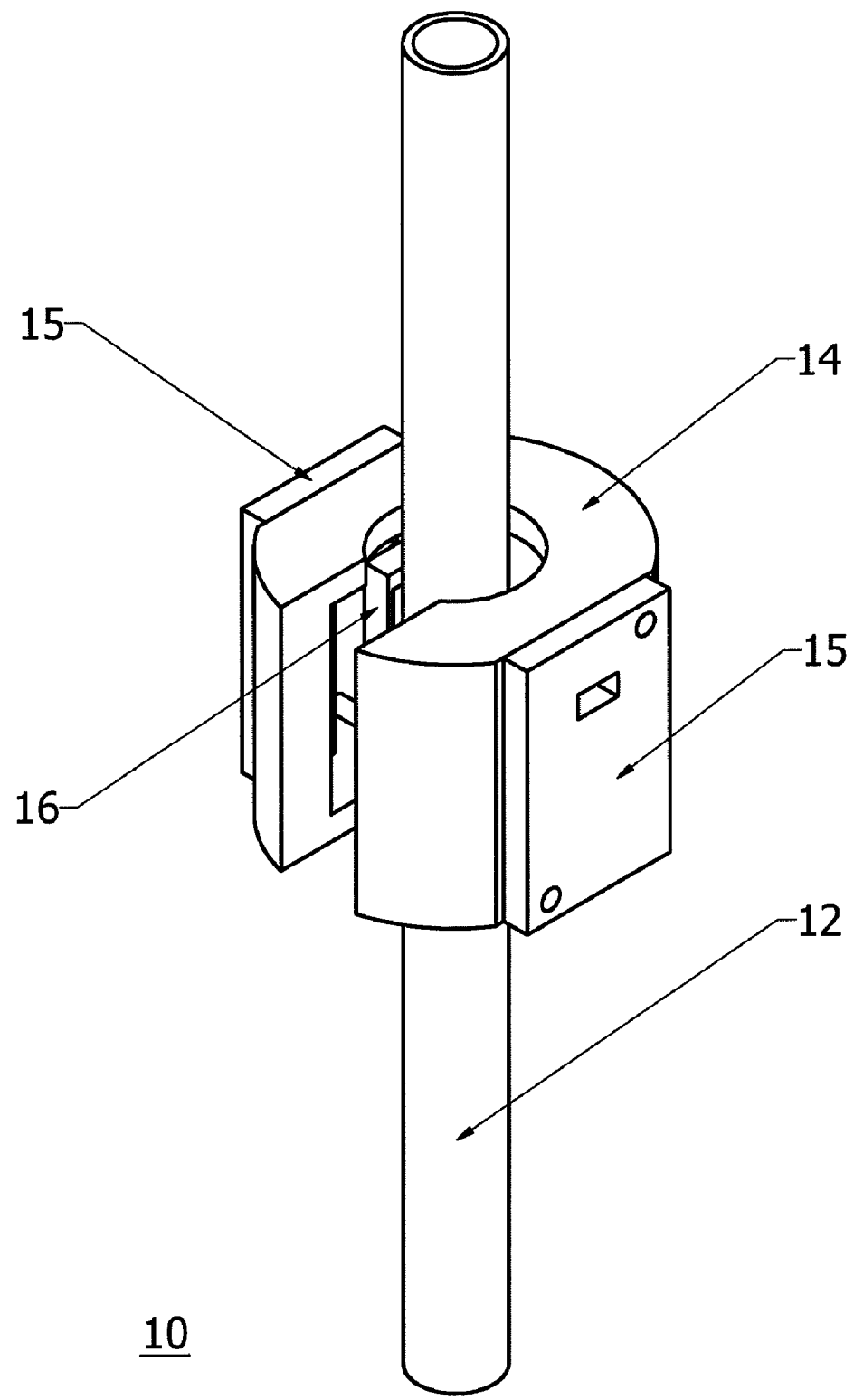
FIG. 1 illustrates a first exemplary embodiment of the present invention utilizing the RF source and the RF detector elements.

FIG. 1 illustrates a first preferred exemplary embodiment of the present invention, which is shown generally at 10. The arrangement illustrated in FIG. 1 is suitable for a wide variety of applications including fluid flow sensors, fluid level sensors, solid product detectors and pill counters. It should be recognized that these are just a few of the examples of applications for this arrangement. In this first preferred exemplary embodiment, a tube member 12, preferably comprised of a nonconductive material such as plastic, and the like, provides a transmission channel for a liquid, solid or gas.

An RF energy emitter/receiver structure housing 14 preferably surrounds or at least substantially surrounds the tube member 12. In illustration of FIG. 1, the housing 14 is a C-shaped generally cylindrical body located around the tube member 12. The RF energy emitter/receiver structure housing 14 may be comprised of a conductive material such as machined aluminum or any other conductive structure and is preferably comprised of molded plastic with a coating of chrome on the internal side walls of plastic material. The conductive housing limits spurious emissions from the device and reduces extraneous RF noise thereby improving accuracy and the ability of the system to achieve finer resolution. It should be recognized by those skilled in the art at that an alternate two-piece construction or multiple piece construction could be provided, which simply snap fits over the nonconductive tube member 12.

The RF energy emitter/receiver structure housing 14 is preferably provided with access plates 15 on opposed sides of the RF energy emitter/receiver structure housing 14. The opening in the housing structure 14 also provides a view of the RF energy emitter structure 16 which is described in more detail below.

Figure 2:
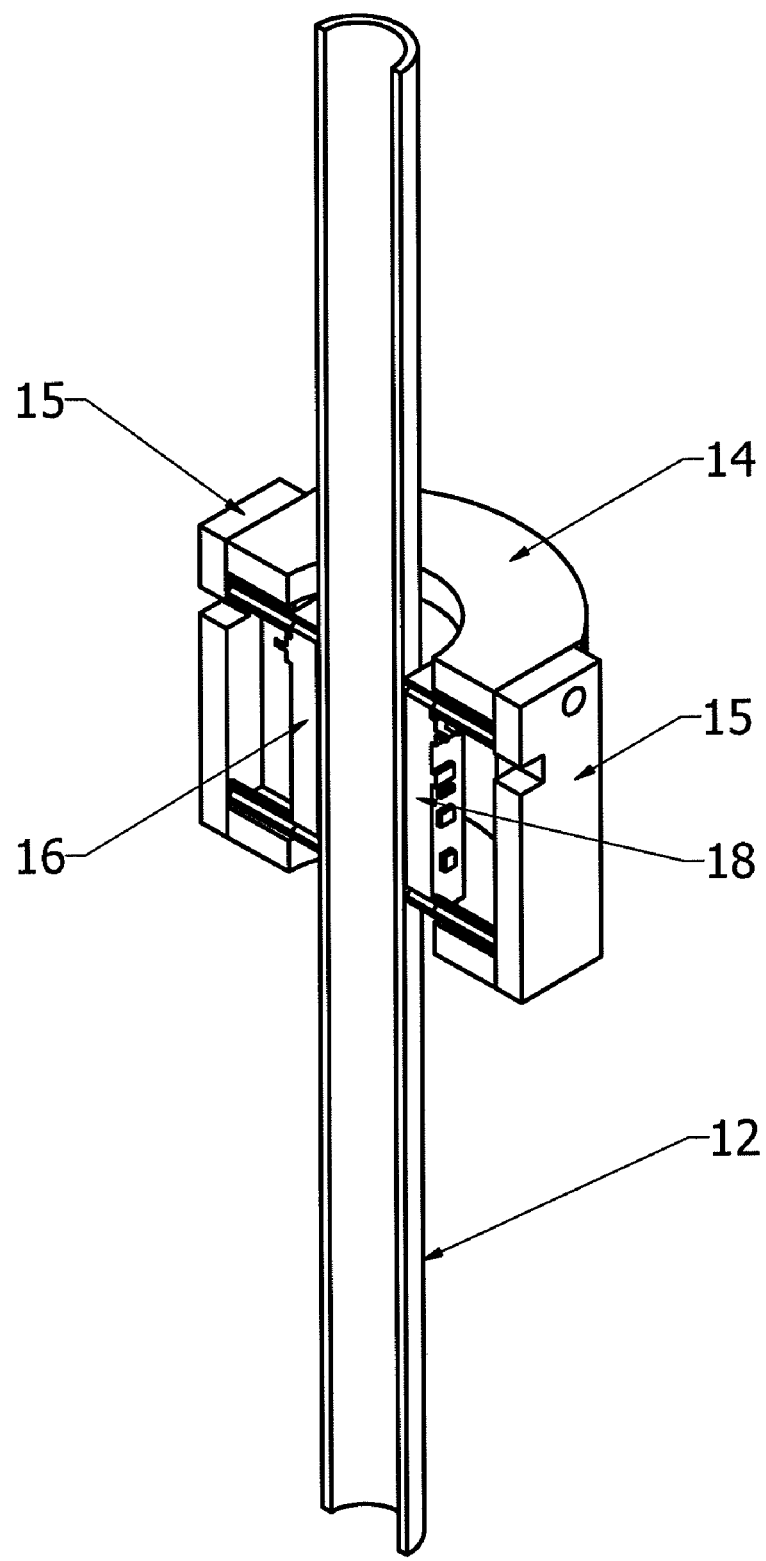
FIG. 2 illustrates a cutaway side view which illustrates the RF source and the RF detector elements of FIG. 1.

FIG. 2 is a cutaway illustration of the RF energy emitter/receiver structure housing 14 and the nonconductive tube member 12, which shows the relationship between the nonconductive tube member 12 as well as the RF energy emitter 16 which is provided on a first side of the solid, liquid or gas transmission channel 12 and an RF energy receiver/detector 18 that is provided at an opposite side of the solid liquid or gas fluid channel 12.

The RF energy emitter 16 either continuously or periodically emits RF energy which in the preferred exemplary embodiment is in the high-frequency or more preferably ultrahigh frequency signal range. For example, in exemplary embodiment, the RF energy transmission source 16 provides at least a primary output of approximately 2.4 GHz. Those of ordinary skill in the art will appreciate that a wide range of transmission frequencies are possible for utilization in conjunction with the systems and methods of the present invention. The RF energy detector mechanism 18 is located across the solid liquid or gas transmission channel.

Additional circuitry is provided either within the housing 14 or remotely from the housing 14 which provides a signal indicative of whether a solid, liquid or gas is present within the space between RF energy emitter 16 and the RF energy receiver/detector 18. This is possible due to the fact that the inventors have discovered that an amount of RF energy transferred from the RF energy emitter 16 structure to the RF energy receiver/detector 18 is altered depending upon whether a solid, liquid or gas is located between RF energy emitter 16 and the RF energy receiver/detector 18.

Circuitry which is described in more detail below is provided for ascertaining whether or not a solid, liquid or gas is located between RF energy emitter 16 and the RF energy receiver/detector 18. In accordance with the preferred exemplary embodiment, a comparator is preferably utilized in making this determination. More specifically, a voltage corresponding to an amount of detected RF energy is provided and compared with a predetermined triggering or voltage reference level. Those skilled in the art will appreciate that more or less RF energy is transferred from the RF energy emitter 16 and the RF energy receiver/detector 18 depending upon whether a solid, liquid or gas is located there between. Selection of an appropriate reference level input to the comparator is utilized in making the determination as to whether a solid, liquid or gas is located between RF energy emitter 16 and the RF energy receiver/detector 18.

For example, in an embodiment wherein the system is utilized as a fluid level sensor, logic circuitry is provided to indicate that a fluid is no longer present. This can easily be achieved due to the recognition that the transferred RF energy will decrease and therefore the voltage corresponding to the amount of detected RF energy will fall below a predetermined level thereby indicating that the fluid is no longer present between the RF energy emitter 16 and the RF energy receiver/detector 18. The same signal relationship will exist (i.e. a decreasing signal voltage trigger point) when the system is used as a bubble detector for identifying potentially harmful bubbles in intravenous fluid lines. Alternatively, when the system is used as a pill counter, for example, changes in the amount of detected RF energy and corresponding variations in the output voltage from the RF detector can be used to determine when a pill or other solid object passes between the RF energy emitter 16 and the RF energy receiver/detector 18.

Accordingly, those skilled in the art will appreciate that various signal processing arrangements may be provided in different types of applications for determining whether a solid, liquid, or gas is present at a specified location. Those skilled in the art will also appreciate that either logic circuitry or a microprocessor may be utilized for determining whether an output signal corresponding to the amount of detected RF energy falls above or below a predetermined threshold. As noted, depending upon the particular implementation this information can be used to determine whether or not a variety of different events have occurred.

FIG. 3A illustrates a perspective view of an exemplary circuit board for use conjunction with the present invention. In the preferred exemplary embodiment, the RF energy emitter 16 and at least most of its required circuitry 22 is formed on a single printed circuit board. The same is also true of the RF energy receiver/detector 18 as at least most of its required circuitry 22 is formed on a single printed circuit board.

Figure 3:
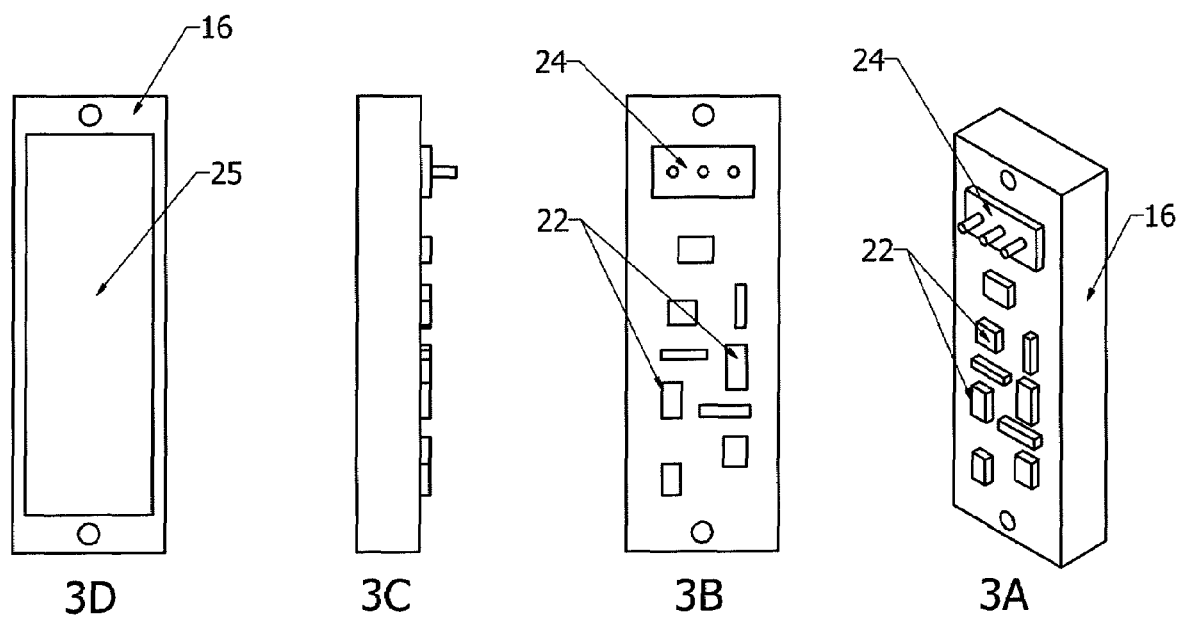
FIG. 3A illustrates a perspective view of an exemplary circuit board for use in conjunction with the present invention.
FIG. 3B illustrates a top plan view of an exemplary circuit board for use in conjunction with the present invention.
FIG. 3C illustrates a side view of an exemplary circuit board for use in conjunction with the present invention.
FIG. 3D illustrates an antenna or emitter/receiver portion provided on the printed circuit board for use in conjunction with the present invention.

More specifically, as shown in FIG. 3A, the RF emitter 16 preferably includes an appropriately tuned oscillator including all of the necessary transistors, capacitors and resistors 22 on a first side of the print circuit board as shown in FIG. 3A. It should be recognized that the subject matter illustrated in FIGS. 3 A-D applies to both the RF energy emitter 16 and the RF energy receiver/detector 18. The illustrations of FIGS. 3A-D are meant to be generic illustrations of either the RF energy emitter 16 or the RF energy receiver/detector 18.

FIGS. 3A and 3B also illustrates a connector 24 which in the preferred exemplary embodiment is used to provide power and ground connections or any other appropriate voltage levels as well as a signal output.

It should also be recognized that it is not necessary to have at least most of the circuitry associated with the RF energy emitter 16 and the RF energy receiver/detector 18 on their respective printed circuit boards. As detailed below, a coaxial cable may physically connect a separate RF source to the actual emitter structure and the RF energy receiver can be connected to the RF detector via a similar coaxial cable.

A via or through hole connection is preferably provided in the print circuit board to transmit the RF energy from a first side of the circuit board at which the transistors, capacitors and resistors 22 are located to an opposite side thereof. The same is also true for the RF receiver/detector when the detector circuitry is physically located on the same circuit board as the RF energy receiving element. FIG. 3B illustrates a top plan view of an exemplary circuit board for use in conjunction with the present invention which illustrates the transistors, capacitors and resistors 22. FIG. 3C illustrates a side view of an exemplary circuit board for use in conjunction with the present invention. FIG. 3D illustrates an antenna or electromagnetic energy emitter or receiver portion 25 provided on a printed circuit board for use in conjunction with the present invention. The antenna or electromagnetic energy emitter or receiver portion 25 is conveniently formed as a conductive metal layer on the circuit board. In the preferred exemplary embodiment, the circuit board is preferably approximately 0.3 by 0.9 inches. The electromagnetic energy emitter or receiver portion 25 is preferably 0.3×0.7 inches.

Figure 4:
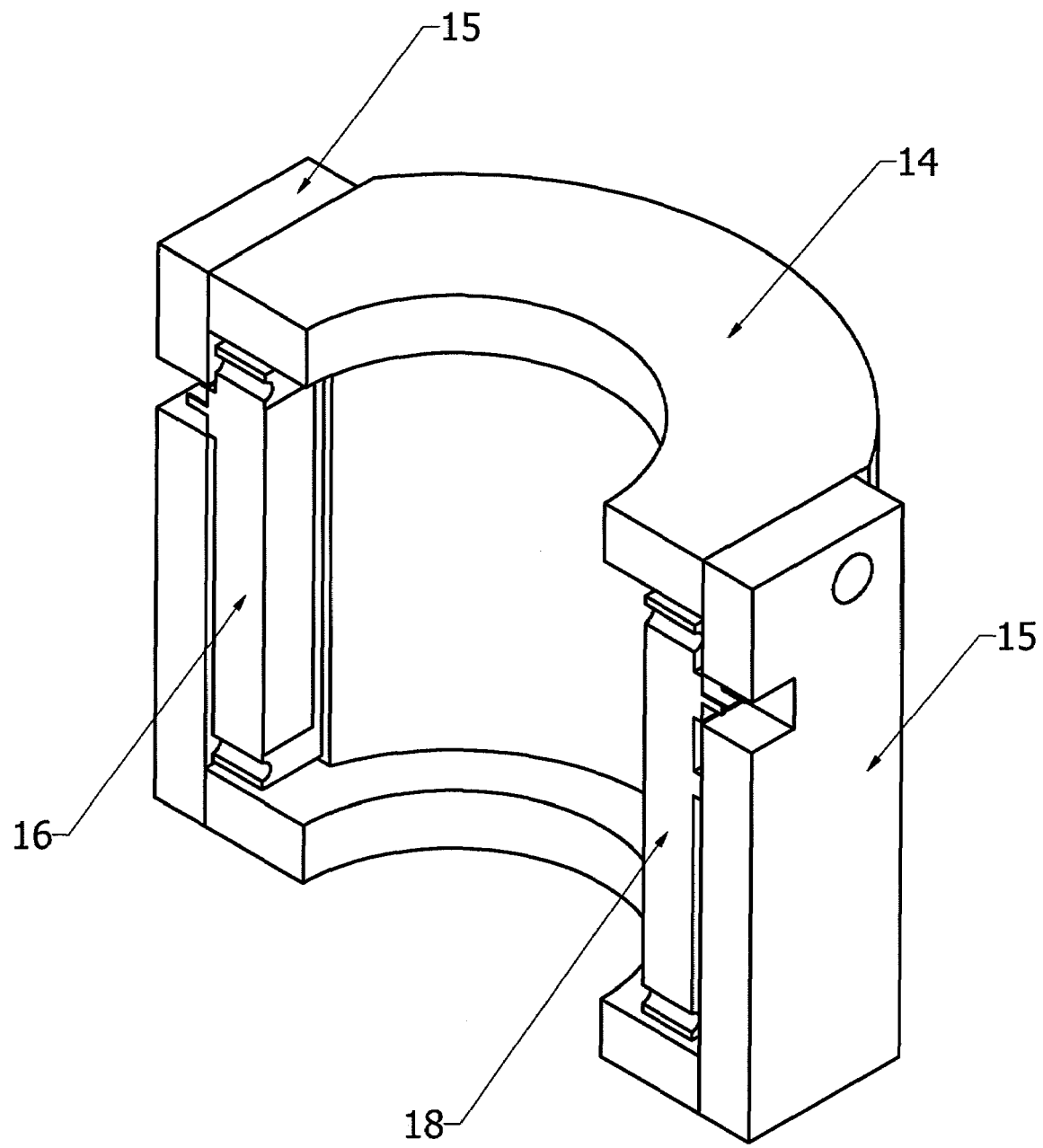
FIG. 4 illustrates the details of an exemplary RF emitter/RF detector assembly enclosed within its cavity.

FIG. 4 is a cutaway illustration of the RF energy emitter/receiver structure housing 14 and the RF energy emitter 16 and the RF energy receiver/detector 18. FIG. 4 illustrates in detail the preferred relative physical relationship between the RF energy emitter 16 and the RF energy receiver/detector 18. More specifically, the RF energy emitter 16 and the RF energy receiver/detector 18 are preferably diametrically opposed across the physical space within which the solid, liquid or gas to be detected is transmitted. The actual physical spacing between the RF energy emitter 16 and the RF energy receiver/detector 18 is not critical but it is preferred that they are in very close proximity to the physical space within which the solid, liquid or gas to be detected is transmitted. It should be recognized that the solid, liquid and gas sensing systems and methods of the present invention do not rely upon far field RF transmission from one antenna to another. Rather, it is the RF coupling between the closely located emitter and receiver structures which is used in determining the presence of a solid, liquid or gas in the space between the RF energy emitter 16 and the RF energy receiver/detector 18.

Figure 5:
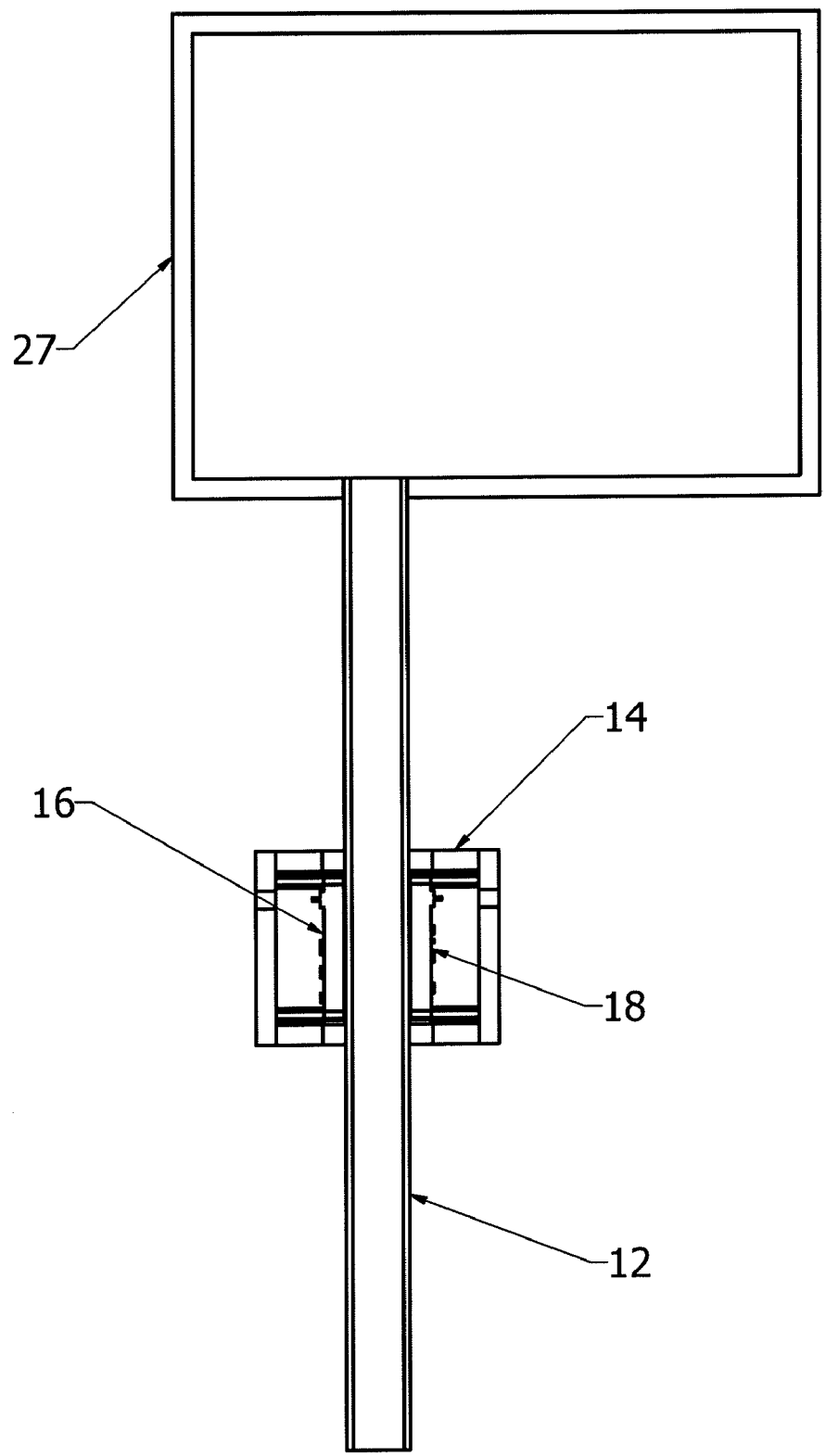
FIG. 5 illustrates use of the RF emitter/RF detector as an out of product sensor.

FIG. 5 illustrates an exemplary embodiment of the present invention wherein the RF energy emitter 16 and the RF energy receiver/detector 18 are employed as an out of product sensor in a vending machine system. For example, this arrangement may be utilized in determining when a coffee machine or soda machine is either running out of or which has run out of the concentrated product to be dispensed. In this embodiment, the RF energy emitter 16 and the RF energy receiver/detector 18 are secured with a fluid transmission channel 12 located there between. The fluid transmission channel 12 is connected to a product containment structure 27. As described above, a change in the coupled RF energy between the RF energy emitter 16 and the RF energy receiver/detector 18 is used in determining if the product containment structure 27 no longer contains fluid. Either a microprocessor or logic circuitry may be used to generate an appropriate electrical signal when this occurrence is determined. This signal may be transmitted to a remote location via an RF transmitter or a network connection so that the containment structure 27 may be replenished or replaced at an appropriate time.

Figure 6:
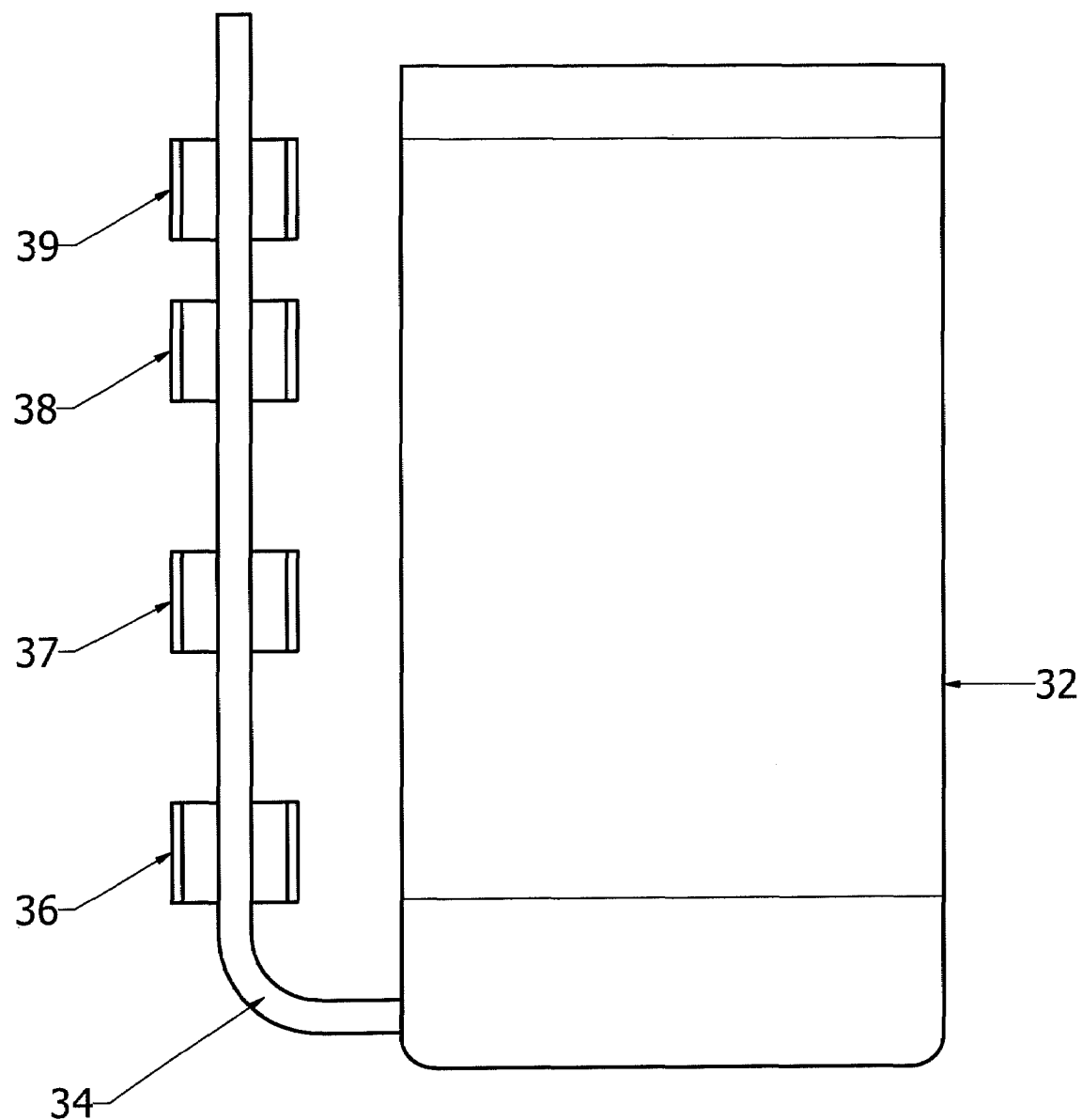
FIG. 6 illustrates the RF emitter/RF detector when utilized as a liquid level sensor.

FIG. 6 illustrates an alternate embodiment of the present invention wherein the systems and methods of the present invention are utilized for determining the level of a fluid within a tank which is shown generally at 30. In the embodiment of FIG. 6, a fluid tank 32 contains a liquid and a fluid transmission channel 34 extends vertically along a side of the fluid tank 32. A plurality of fluid level sensors 36, 37, 38, 39, are arranged at separate vertical locations along the fluid transmission channel 34. In this embodiment, changes in the detected RF signal level for each of the fluid level sensors may be used to determine a current level for the fluid within the fluid tank 32. The outputs of these signals may be transferred to logic circuitry and/or a microprocessor which may be utilized to generate a fluid level signal.

Figure 7:
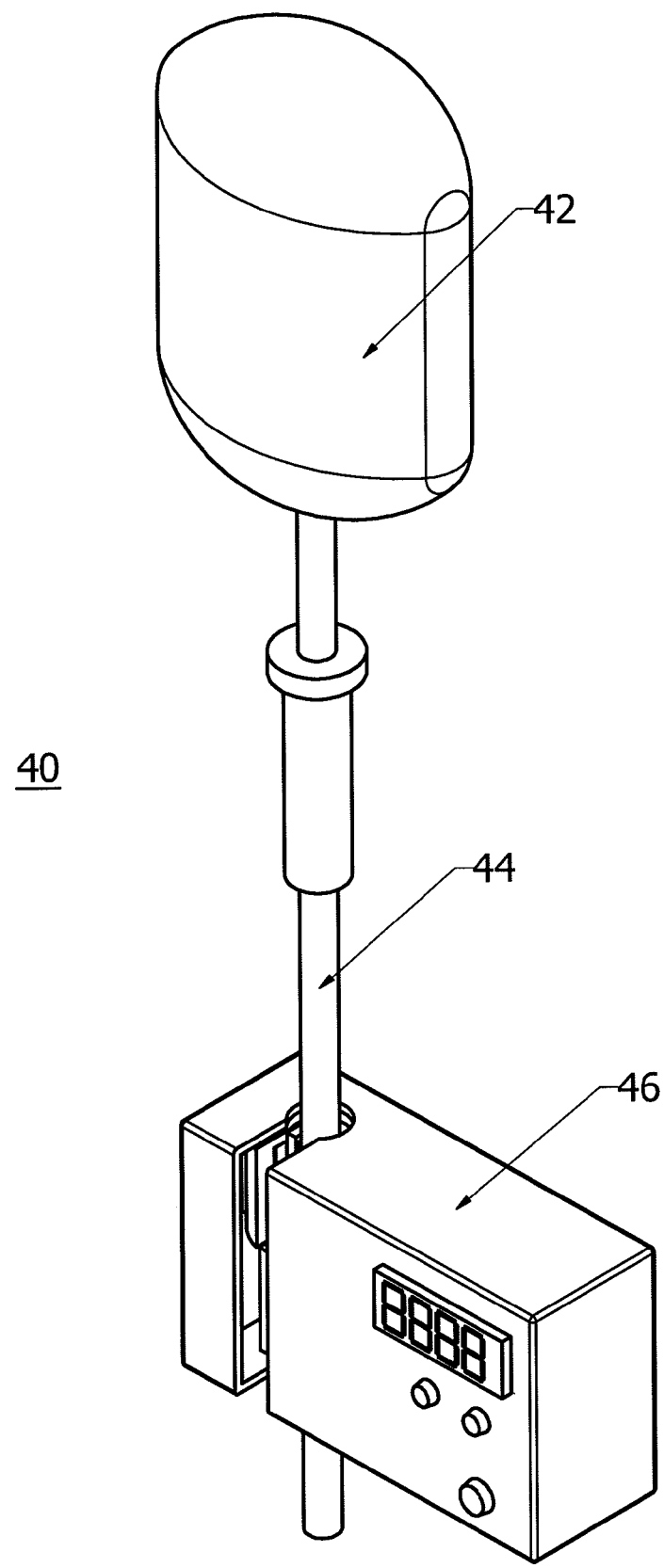
FIG. 7 illustrates use of the RF emitter/RF detector as an air bubble or contaminant sensor for an infusion system.

FIG. 7 illustrates an alternate preferred exemplary embodiment of the present invention which is shown generally at 40 wherein the systems and methods of the present invention are utilized in an intravenous fluid administration system for determining when a potentially hazardous gas bubble is present in an intravenous fluid line that is connected to a patient. In this embodiment, an intravenous fluid source 42 is connected to a patient via an intravenous fluid transmission line 44 and a flow monitoring mechanism 46 is preferably provided for determining when a potentially harmful gas bubble is passing through the intravenous fluid line. If such an event occurs, the flow monitoring mechanism 46 also preferably incorporates an alarm and an automatic shutoff which prevents the potentially harmful gas bubble from entering a patient.

Figure 8:
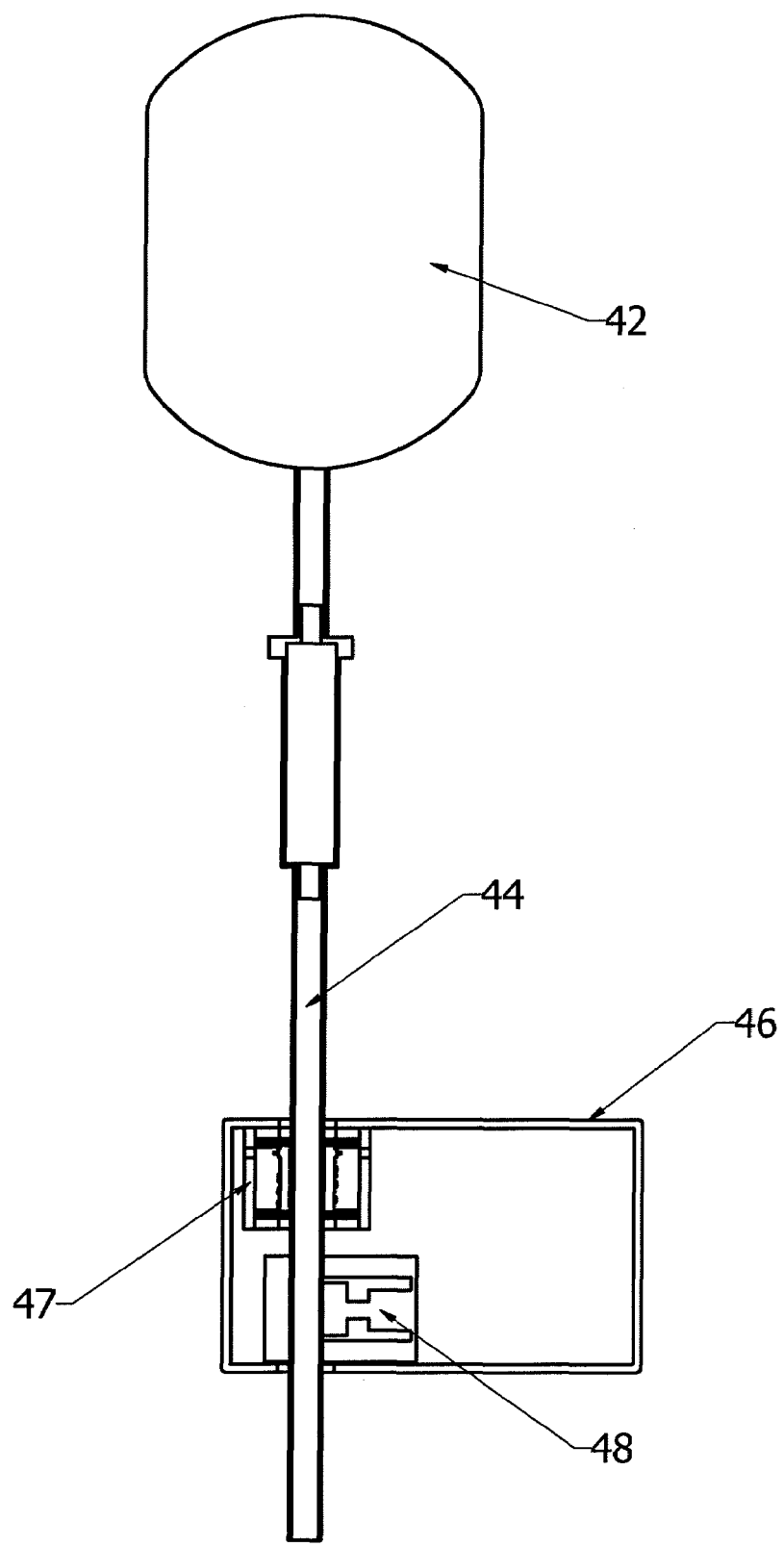
FIG. 8 is a cutaway illustration of the RF emitter/RF detector as an air bubble or contaminant sensor for an infusion system.

FIG. 8 is a cutaway view illustrating the intravenous fluid administration system shown in FIG. 7. In this embodiment, gas bubble detection circuitry 47 includes an RF energy emitter 16 and the RF energy receiver/detector 18. During system operation, a potentially harmful gas bubble may be identified by determining that gas is present in the space between the RF energy emitter 16 and the RF energy receiver/detector 18 over a sufficient period of time. It is recognized that it is not uncommon to have air bubbles in intravenous fluid administration lines, however, if they are sufficiently large, they can be hazardous to a patient. Accordingly, depending upon flow rate, the size of a potentially harmful gas bubble may be determined and if gas is present between the RF energy emitter 16 and the RF energy receiver/detector 18 over a sufficient period of time the flow shut off mechanism 48 operates to prevent the potentially harmful gas bubble from entering a patient. Either a microprocessor or logic circuitry may be utilized for generating a signal which triggers the flow shutoff mechanism 48.

By utilizing the technology of the instant invention, it is possible to not only determine whether a gas bubble is present in an intravenous fluid line but it is also possible to determine and characterize the size of the gas bubble. This may be important in certain applications where information concerning an aggregate amount of gas bubbles is desired to be known. The inventors have discovered that it is possible to ascertain the relative size of the gas bubble present in an intravenous fluid line by analyzing an amount of RF energy detected by the system. More specifically, the inventors have discovered that a smallest amount of RF coupling and therefore the smallest signal occurs when the gas bubble present in the intravenous fluid line is approximately the size of the antenna/emitter structure and receiver element physical dimensions. When no gas bubble is present and only liquid fills the intravenous fluid line between the RF emitter structure and RF receiver element, the greatest amount of coupling is realized and the strongest RF signal is detected.

It is possible to use the systems and methods of the present invention to determine a volume of a gas bubble present in an intravenous fluid line by providing a correlation between the amount of RF energy received by the system with the size of the gas bubble present in the line. Those skilled in the art will appreciate that a 1 $cm^3$ bubble located between the emitter structure and the receiver element will result in a predictable reduction in the amount of detected RF energy. A data table providing this correlation based on experimentation with a particular system having a certain size intravenous line and separation between the emitter and RF receiving element may be utilized to accurately characterize the size of a gas bubble present in an intravenous fluid line. Those skilled in the art will also recognize that is not necessary to use a data table and it may be also possible to rely upon a calculation of the gas bubble size based upon a determined mathematical relationship between received signal strength and the volume of gas bubble.

It should also be recognized that it is also possible to provide an aggregate calculation to provide a total amount of gas bubble volume based upon known fluid transmission rates.

Figure 9:
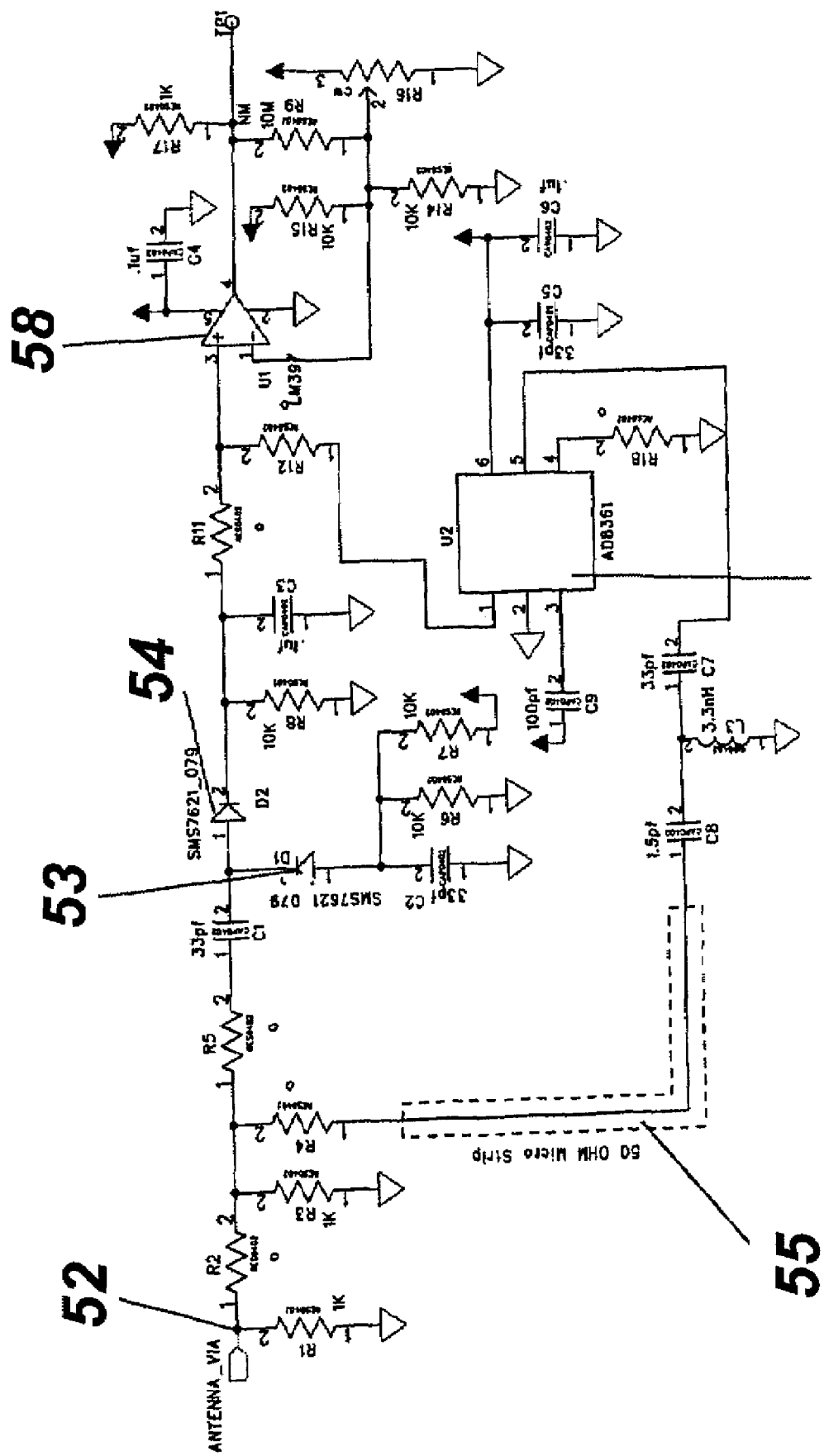
FIG. 9 is a schematic diagram which illustrates the RF detector.

FIG. 9 is a schematic diagram which illustrates a preferred circuit and arrangement for implementing the RF detector which is shown generally at 50. In accordance with the preferred exemplary embodiment as shown in FIGS. 3A-D, this circuit is preferably located on a first side of a printed circuit board and the electromagnetic energy receiver structure is preferably located on an opposite side of the printed circuit board. As noted above, antenna or electromagnetic receiver portion 25 is conveniently formed as a conductive metal layer on one side of the circuit board. In the preferred exemplary embodiment, the circuit board is preferably approximately 0.3 by 0.9 inches. The electromagnetic energy emitter or receiver portion 25 is preferably 0.3×0.7 inches. The schematic diagram illustration of FIG. 9 actually provides two alternate embodiments of the RF detector for the present invention. Antenna or electromagnetic receiver portion 25 which is not shown in this illustration is connected to the circuit at node 52.

A first embodiment employs a simple RF detector element which relies upon Schottky diodes 53, 54 which provide a DC voltage corresponding to an amount of received RF energy. Diodes D1 (53) and D2 (54) are preferably embodied as Alpha Industries model SMS7621_079. The DC voltage output from the diode D2 (54) is applied to a first input of comparator 58. A second input of comparator 58 receives a reference voltage. Those skilled in the art will appreciate that by providing an appropriate reference voltage, the comparator 58 will provide an output indicative of whether a solid, liquid, or gas is present between the between the RF energy emitter 16 and the RF energy receiver/detector 18.

If the diode detectors are utilized for providing the DC voltage corresponding to an amount of received RF energy, the indicated connection via the microstrip line 55 to the RF detector chip 56 is not provided. Furthermore, any of the illustrated circuitry solely relating to the operation of the RF detector chip 56 would not be provided if the Schottky diodes are utilized. Similarly, the RF detector chip 56 is not provided when the diode detectors are utilized. This first embodiment provides a less expensive alternative for determining whether a solid liquid or gas is present. The transmission path through the 50 ohm microstrip line 55 to the RF detector chip 56 is used as an alternate embodiment for providing more precise information. When the alternate embodiment utilizing the RF detector chip 56 is used, the connection via R 5 is not made in the diode detectors 53, 54 are not provided.

In the alternate preferred exemplary embodiment, the RF detector chip 56 is preferably an analog devices model AD8361. In this alternate embodiment, the output from the RF detector chip 56 is applied to a first input of the comparator 58. A second input of comparator 58 receives a reference voltage. Those skilled in the art will appreciate that by providing an appropriate reference voltage, the comparator 58 will provide an output indicative of whether a solid, liquid, or gas is present between the between the RF energy emitter 16 and the RF energy receiver/detector 18.

In yet another alternate arrangement, the comparator 58 may be replaced with an amplifier for applications where it is desired to achieve improved analysis of the detected RF energy. For example, when using the technology of the instant invention as a pill counter, amplification of the detected RF energy signal is required due to the brief duration of the signal pulse created when the pill passes between the RF emitter and RF receiver elements. The same is also true when utilizing the present invention for the purpose of determining an aggregate amount of bubbles passing through an intravenous fluid line. Those skilled in the art will appreciate that the specific application of the technology disclosed in the present application will determine which circuit is more appropriate.

Figure 10:
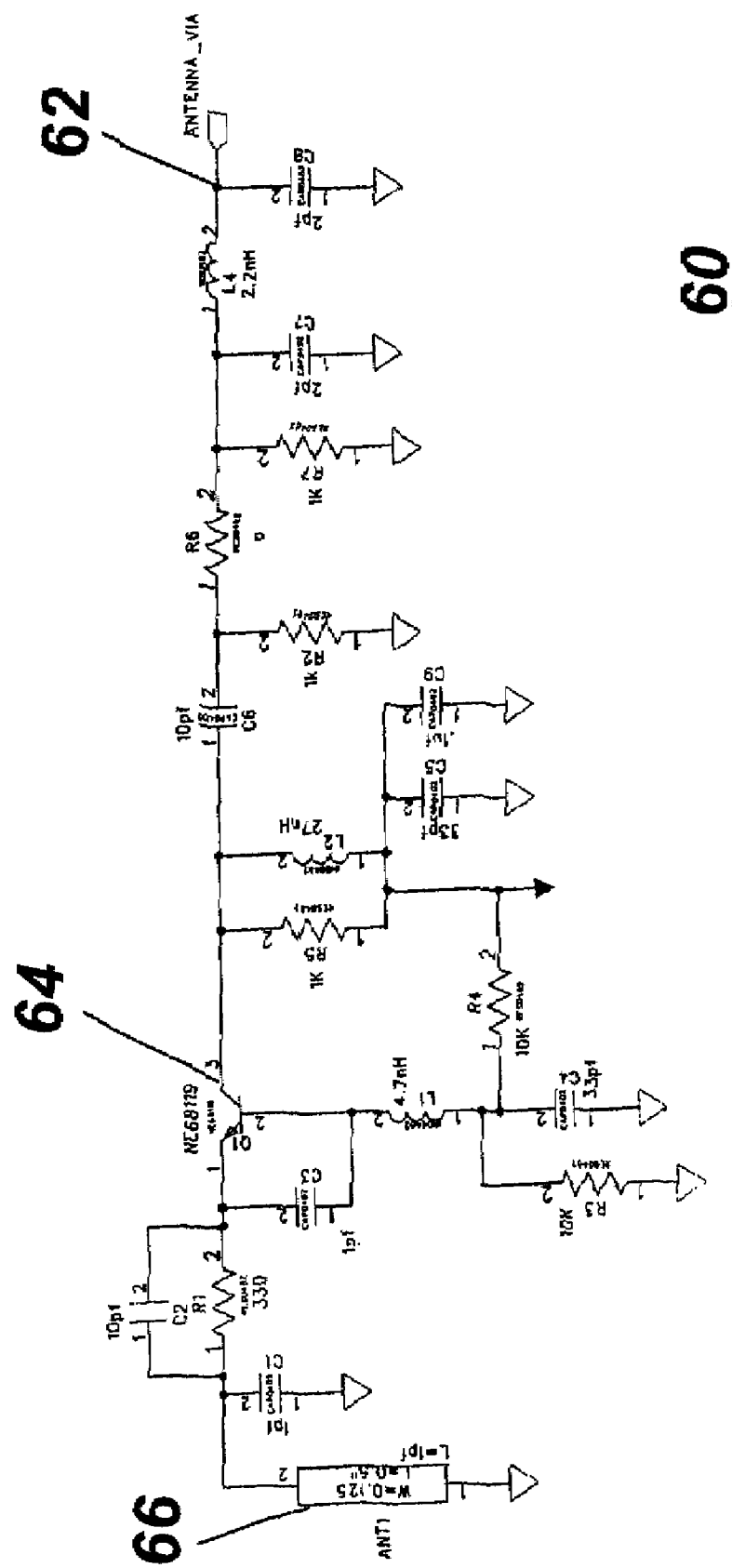
FIG. 10 is a schematic diagram which illustrates the RF emitter.

FIG. 10 illustrates an exemplary embodiment of the RF source circuitry that is shown generally at 60. In accordance with the preferred exemplary embodiment as shown in FIGS. 3A-D, this circuit is preferably located on a first side of a printed circuit board and the electromagnetic energy emitter structure is preferably located on an opposite side of the printed circuit board. As noted above, antenna or electromagnetic emitter portion 25 is conveniently formed as a conductive metal layer on one side of the circuit board. In the preferred exemplary embodiment, the circuit board is preferably approximately 0.3 by 0.9 inches. The electromagnetic energy emitter or receiver portion 25 is preferably 0.3×0.7 inches. Antenna or electromagnetic emitter portion 25 which is not shown in this illustration is connected to the circuit at node 62.

Those skilled in the art will appreciate that a variety of different RF energy oscillator designs may be utilized. The present oscillator design is a convenient and economic alternative. In this design, a high-frequency transistor 64 embodied as a model NE68119 manufactured by Celeritek is used in generating the RF energy. Tuning of the output is achieved by altering the physical dimensions of the microstrip conductive layer 66. Various other circuit elements are provided for filtering of the output as recognized by those of ordinary skill in the art. As noted above, the preferred operating range for the RF source is in the high-frequency or ultrahigh frequency range and is preferably greater than 1 GHz and more preferably the output is at frequency range of operation around 2.4 or 2.5 GHz. Those skilled the art will recognize that other frequencies higher and/or lower than these ranges may also work suitably with the technology disclosed in the instant patent application.

Figure 11:
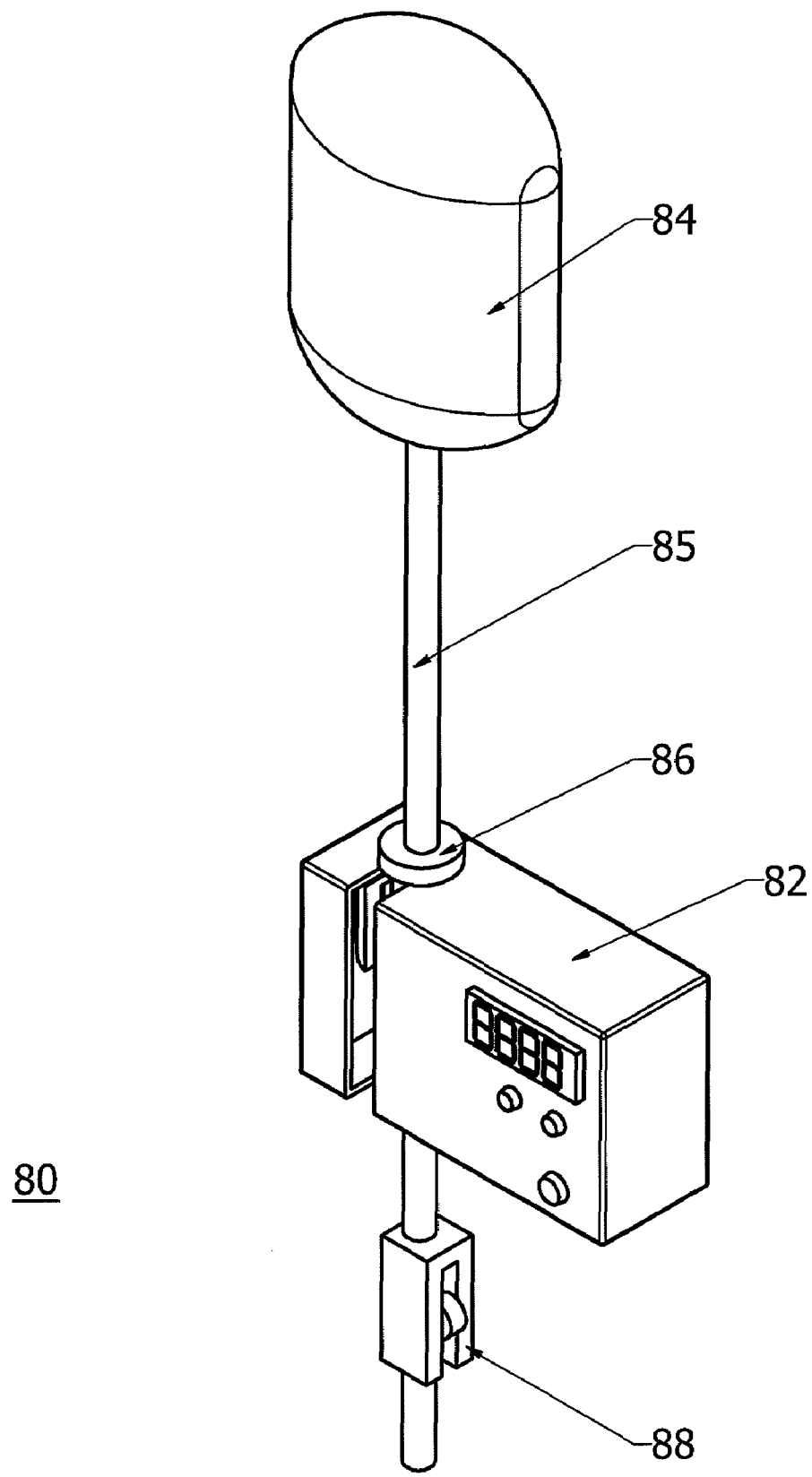
FIG. 11 illustrates use of the RF emitter/RF detector as fluid flow rate sensor embodied in an intravenous fluid system.

FIG. 11 illustrates an alternate preferred exemplary embodiment of the present invention wherein the solid, liquid, or gas sensing mechanism operates as a fluid flow rate sensor in an intravenous fluid administration system which is shown generally at 80. In this alternate preferred exemplary embodiment, the housing 82 preferably encloses the RF source and emitter structure as well as the receiving element and RF detector circuitry. An intravenous fluid source 84 is provided and an intravenous fluid line 85 transfers the intravenous fluid into the patient. The system housing 82 preferably includes a slotted region for receiving a portion of the intravenous fluid line 85 and a drip cup portion 86. A fluid flow adjustment mechanism 88 is also preferably provided.

Figure 12:
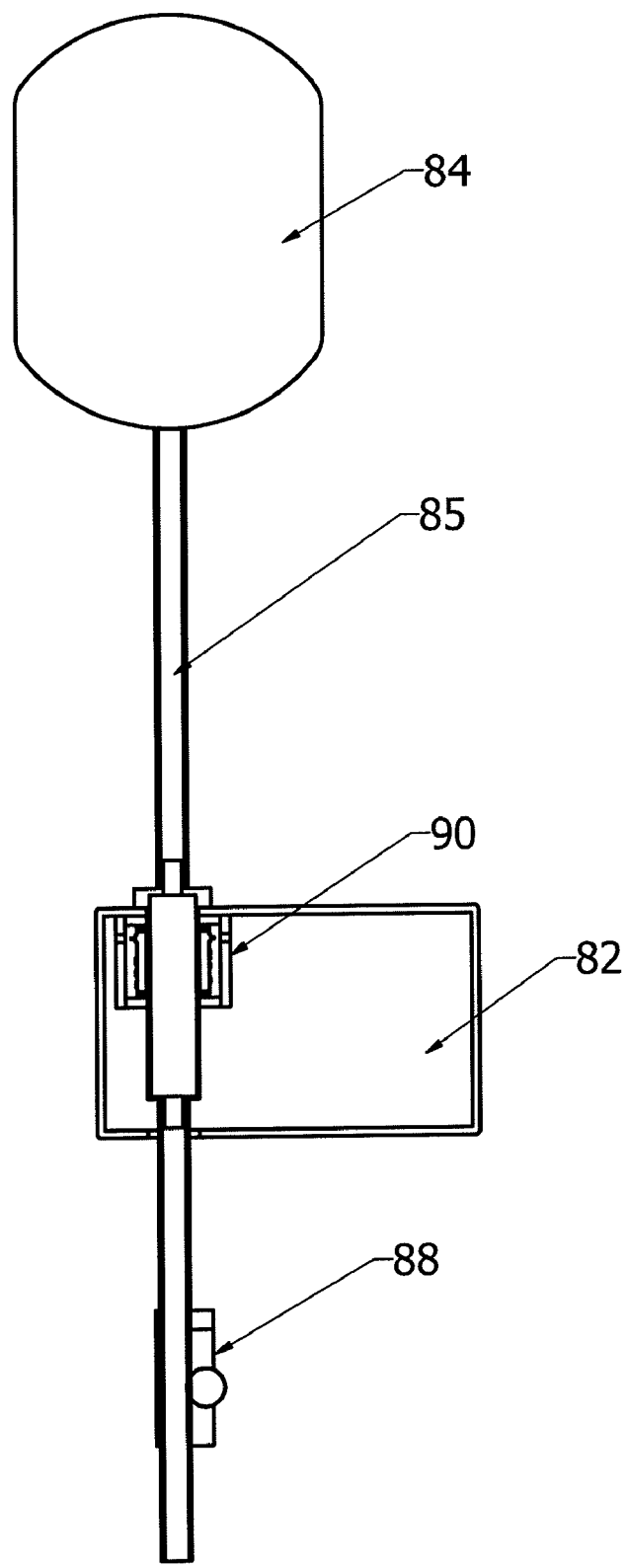
FIG. 12 is a cutaway illustration of the RF emitter/RF detector as fluid flow rate sensor embodied in an intravenous fluid system.

FIG. 12 is a cutaway illustration of the fluid flow rate sensor shown in FIG. 11. This cutaway view provides a more detailed illustration of the relationship between the source/emitter and RF receiving element/RF detector structures 16, 18 and the drip cup 86. As shown in FIG. 12, the drips of fluid traveling toward the patient pass between source/emitter and RF receiving element/RF detector structures 16, 18. The signal output corresponding to an amount of received and detected RF energy may be correlated with a fluid flow rate. For example, signal pulses or temporary rises in an output signal level indicate the passage of a drip of fluid between the RF receiving element/RF detector structures 16, 18. An amount of fluid drips passing into the drip cup in a given amount of time may be correlated with a fluid flow rate for the system. The determined fluid flow rate is preferably displayed via a liquid crystal panel. The system may incorporate alarms which indicate when a determined flow rate is not within a predetermined range of a desired fluid flow rate.

Figure 13:
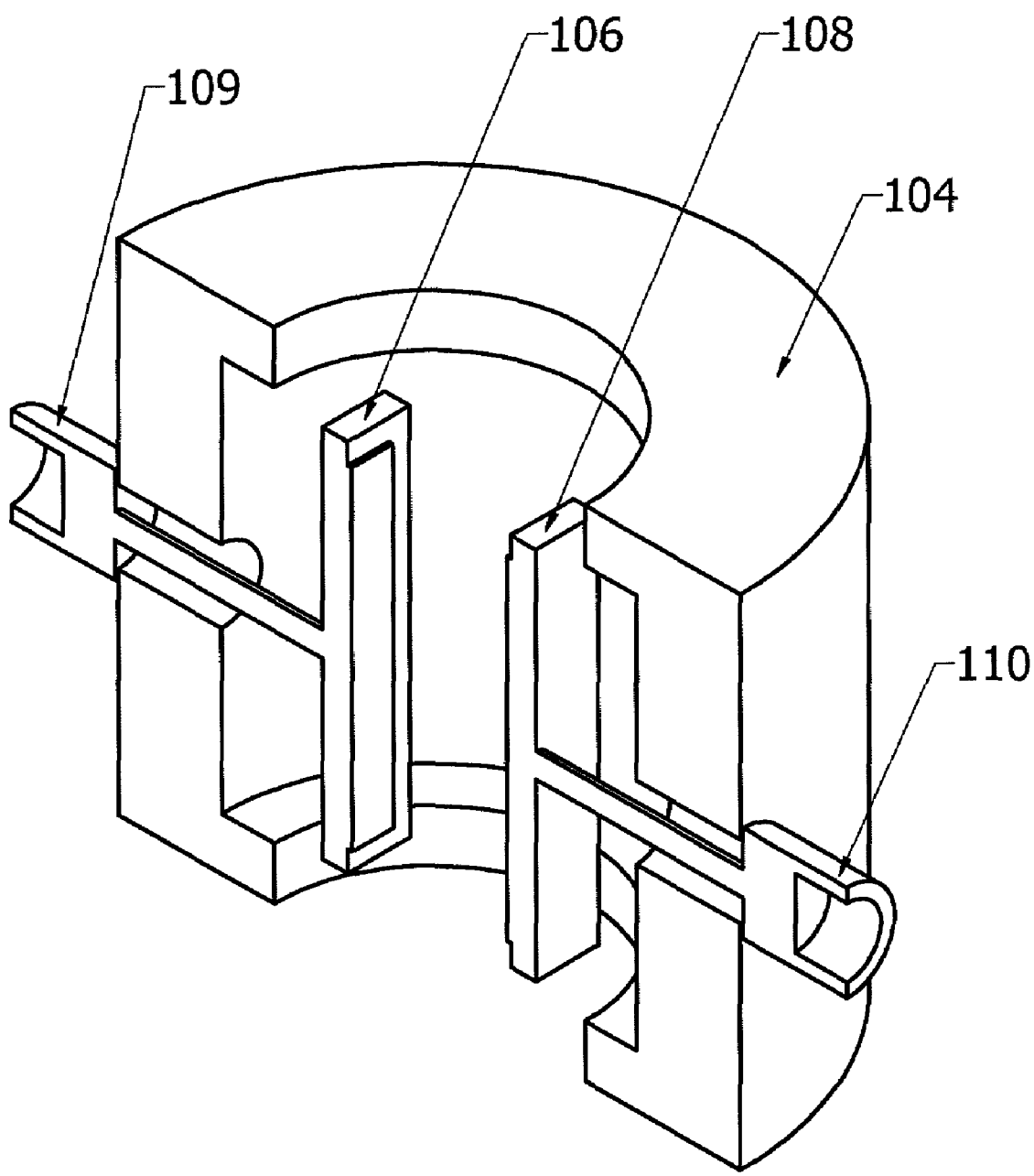
FIG. 13 illustrates the emitter and receiver structures provided on a printed circuit board for use in conjunction with the present invention wherein the RF source circuitry and RF detector circuitry are located remotely from the emitter and receiver elements.

FIG. 13 illustrates an alternate preferred exemplary embodiment of the present invention wherein the circuitry for the RF source and the RF detector are located remotely which is shown generally at 100. In this alternate preferred exemplary embodiment, a housing 104 which is preferably formed in the same manner as the housing of the embodiments described above encloses an RF emitter element 106 and an RF receiving element 108. Shielded coaxial signal lines 109 and 110 transfer the RF energy to/from the RF emitter element 106 and an RF receiving element 108. In this alternate exemplary embodiment, the circuitry for the RF source and the RF detector are located remotely from the actual location at which the solid, liquid or gas is being detected. Those skilled in the art will appreciate that the RF emitter and receiver element structure may alternately be embodied as a single piece of a conductive material such as, for example, a conductive strip or metal wire connected to the coaxial signal lines 109 and 110 and that a printed circuit board is not required.

Figure 14:
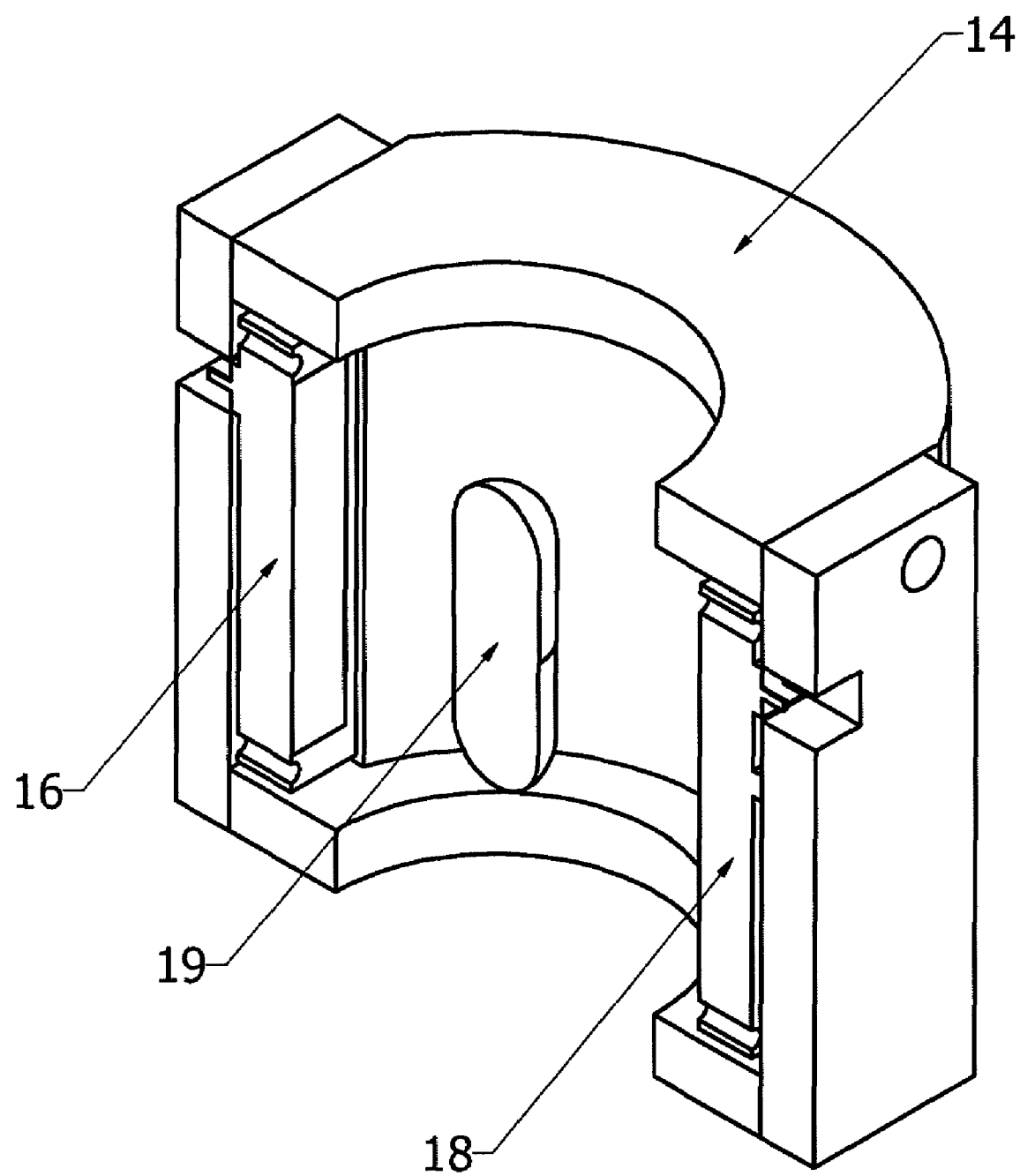
FIG. 14 illustrates the RF emitter/RF detector as a pill counter.

FIG. 14 illustrates an alternate preferred exemplary embodiment of the present invention wherein the system and methods of the present invention are used to provide either a pill counting mechanism and/or a system for verifying whether a pill or other solid object transmitted through the transmission channel is defective and/or whether it is the correct pill or other product passing through the transmission channel. As illustrated in FIG. 14, a pill 19 passes between the RF emitter and receiver element structures 16, 18. By analyzing the signal output provided by the RF detector, it is possible to determine whether a pill passing through the transmission channel is defective and/or whether the pill has a signal corresponding with a known signal for the pill.

In this alternate preferred exemplary embodiment, it is preferred that a data table or other memory construct be provided with information concerning an expected range of signals for undamaged pills or other products passing through the transmission channel between the RF emitter and receiver element structures 16, 18. This data may be generated by analysis of experimental results reviewing typical changes in the detected RF energy signal for known good pills or other products passing through the transmission channel. In this alternate embodiment, a signal corresponding to the detected amount of RF energy may be compared with a data table or other range of expected values for the signal pulse generated when the pill or other product passes through the transmission channel. If an actual detected value falls outside of a predetermined range, the system is able to determine that the pill or other product is either defective or is not the correct pill or product that was expected. This information can be very helpful in the pharmaceutical industry for solid pharmaceutical packaging implementations.

As noted above, the radiating element and the receiving structure is each approximately 2 cm in length for the preferred embodiment which is much smaller than the free-space wavelength of the driving RF source and they are enclosed in a small metallic RF cavity or shielded or conductive housing as noted. The physical dimensions may also be smaller or larger depending upon the selected application and the source wavelength. The spacing between the emitter and receiving elements to the inner walls of the RF cavity is very small compared to the length of free-space wavelength of the RF driving source. Typically this distance is preferred to be less than one centimeter. Also, the spacing between the radiating and receiving element may be about 1 cm which is also much smaller than the free-space wavelength of the RF driving source. It is preferred that this distance be substantially less than one wavelength for the source in free space.

Under these conditions the electromagnetic energy is not propagating in space when a nonmetallic tube is inserted in the detector, the electromagnetic (EM) energy is still not coupling to the receiving antenna and no signal is measured at the output of the RF power detector. But when the tube is filled with liquid, the EM energy from the radiating element is coupled to the receiving element and a large signal is measured at the output of the RF power detector. In most applications the RF source and RF detector are on all the time and a microprocessor is used to analyze the output signal from the RF detector. The microprocessor samples the detector output signal at a rate of 100 to 300 Hz. depend on the application.

In situations where it is desired to increase the sensitivity of the measurements (when the output signal from the RF detector is small and the noise level is changing randomly) the detector will stay on all the time while the RF source will be modulated at 50% duty cycle where the time of one cycle is smaller or equal to the signal width. During the time when the RF source is off, the detector will measure the noise level while during the time of the cycle when the RF source is on, the detector will measure the signal plus the noise. By subtracting the measured signal during the time the RF is off from the measured signal when the RF is on, it is possible to calculate the value of the signal level only. For example; if the signal width is 100 msec it is preferred to modulate the RF source at 50% duty cycle 50 msed on and 50 msec off.

Other applications

Dialysis System:

The systems and methods of the present invention can be used in dialysis system to detect the present of gases bubbles in the recirculation blood. It can also be used to detect solid objects floating in the recirculation blood like blood clot. An appropriate order may be sounded if such a situation is detected.

Automobile Industry:

The systems and methods of the present invention may be used to detect fluid in a nonmetallic tubing or the presence of an air bubble or foreign objects in the fluid. The systems and methods of the present invention provide an excellent sensor for the different fluids in the car engine like; fuel flow to the injectors, oil flow, cooling water flow.

Those skilled in the art will recognize that these are but a few examples and the technology of the instant invention has numerous applications. Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

The invention claimed is:

1. A system for determining the presence and/or absence of a solid, liquid or gas within a physical space comprising:
   an RF energy signal source;
   an RF energy emitter;
   an RF energy receiving element;
   an RF energy detector providing a signal corresponding to an amount of RF energy received from the RF energy emitter;
   circuitry for providing a signal indicating whether a solid, liquid or gas is located in a space between the RF energy emitter and the RF energy receiving element at a given time; wherein the RF energy emitter and RF energy receiving element are located on opposite sides of a channel within which the solid, liquid or gas is located, the RF energy being transferred between the RF energy emitter to the RF energy receiving element via a near field effect transmission; and wherein the system determines when a vending system is out of product.

2. The system for determining the presence and/or absence of a solid, liquid or gas within a physical space according to claim 1, wherein the RF energy signal source and RF energy emitter are on a common circuit board.

3. The system for determining the presence and/or absence of a solid, liquid or gas within a physical space according to claim 1, wherein the RF energy receiving element and RF energy detector are on a common circuit board.

4. The system for determining the presence and/or absence of a solid, liquid or gas within a physical space according to claim 1, wherein the system determines when a vending system is almost out of product.

5. A method for determining the presence and/or absence of a solid, liquid or gas within a physical space comprising:
   emitting RF energy that is generated by an RF energy signal source;
   detecting an amount of RF energy transferred across the physical space;
   providing a signal corresponding to an amount of RF energy received from an RF energy emitter; and
   providing a signal indicating whether a solid, liquid or gas is located in a space between the RF energy emitter and an RF energy receiving element at a given time based on the signal corresponding to the amount of received RF energy; wherein the RF energy emitter and RF energy receiving element are located on opposite sides of a channel within which the solid, liquid or gas is located, the RF energy being transferred between the RF energy emitter to the RF energy receiving element via a near field effect transmission; and wherein the method determines when a vending system is out of product.

6. The method for determining the presence and/or absence of a solid, liquid or gas within a physical space according to claim 5, wherein the RF energy signal source and RF energy emitter are on a common circuit board.

7. The method for determining the presence and/or absence of a solid, liquid or gas within a physical space according to claim 5, wherein the RF energy receiving element and an RF energy detector are on a common circuit board.

8. The method for determining the presence and/or absence of a solid, liquid or gas within a physical space according to claim 5, wherein the method determines when a vending system is almost out of product.

* * * * *